(12) United States Patent
Griffin et al.

(10) Patent No.: US 12,357,414 B2
(45) Date of Patent: Jul. 15, 2025

(54) SYSTEMS AND METHODS FOR AN AUTOMATIC PULLBACK TRIGGER

(71) Applicant: LightLab Imaging, Inc., Westford, MA (US)

(72) Inventors: Christopher E. Griffin, Wilton, NH (US); Joel M. Friedman, Andover, MA (US); Ashley Netravali, Littleton, MA (US); Lingfa Yang, Concord, MA (US)

(73) Assignee: LightLab Imaging, Inc., Westford, MA (US)

( * ) Notice: Subject to any disclaimer, the term of this patent is extended or adjusted under 35 U.S.C. 154(b) by 604 days.

(21) Appl. No.: 17/685,034

(22) Filed: Mar. 2, 2022

(65) Prior Publication Data
US 2022/0280259 A1  Sep. 8, 2022

Related U.S. Application Data

(60) Provisional application No. 63/155,833, filed on Mar. 3, 2021.

(51) Int. Cl.
*A61B 90/00* (2016.01)
*G06T 7/13* (2017.01)
*G06T 7/136* (2017.01)

(52) U.S. Cl.
CPC ............ *A61B 90/37* (2016.02); *G06T 7/13* (2017.01); *G06T 7/136* (2017.01);
(Continued)

(58) Field of Classification Search
CPC ............ A61B 90/37; A61B 2090/3735; A61B 5/0261; A61B 5/027; A61B 5/02007;
(Continued)

(56) References Cited

U.S. PATENT DOCUMENTS

| 8,323,273 | B2 * | 12/2012 | Rylander | A61B 5/0071 606/9 |
| 10,852,291 | B2 * | 12/2020 | Seibel | G01N 21/59 |

(Continued)

OTHER PUBLICATIONS

Karmakar A. et al. "Framework for lumen-based nonrigid tomographic co-registration of intravascular images" 2022 Society of Photo-Optical Instrumentation Engineers (SPIE); Journal of Medical Imaging, Feb. 25, 2022 (Year: 2022).*

(Continued)

*Primary Examiner* — Mia M Thomas
(74) *Attorney, Agent, or Firm* — Lerner David LLP

(57) ABSTRACT

Aspects of the disclosure relate to the identification of when a blood vessel has been sufficiently cleared of blood so as to capture intravascular images of the vessel wall. The disclosed systems and methods allow for the identification of an initial and a final blood clearing based on the identification of edges within scanlines of a plurality of image frames. The edges of a plurality of scanlines may be analyzed to determine an average edge offset for each image frame, and the average edge offsets for a plurality of image frames may be averaged over various time-windows, so as to determine when the initial and final blood clearing events have occurred. Once a final blood clearing event has been identified, the disclosed system may automatically initiate a catheter pullback procedure, so as to capture intravascular images over a length of the vessel that has been sufficiently cleared of blood.

26 Claims, 9 Drawing Sheets

(52) U.S. Cl.
CPC .............. *A61B 2090/3735* (2016.02); *G06T 2207/10101* (2013.01); *G06T 2207/20216* (2013.01); *G06T 2207/30101* (2013.01)

(58) Field of Classification Search
CPC ......... A61B 5/0066; G06T 7/13; G06T 7/136; G06T 2207/10101; G06T 2207/20216; G06T 2207/30101
See application file for complete search history.

(56) References Cited

U.S. PATENT DOCUMENTS

| | | | |
|---|---|---|---|
| 2013/0178916 A1* | 7/2013 | Rylander | A61N 5/0616 607/88 |
| 2013/0310698 A1 | 11/2013 | Judell et al. | |
| 2014/0046146 A1* | 2/2014 | Zurn | A61B 18/20 600/573 |
| 2014/0100440 A1 | 4/2014 | Cheline et al. | |
| 2016/0305762 A1* | 10/2016 | Suter | G01B 9/0209 |
| 2017/0024910 A1* | 1/2017 | Griffin | G06T 11/00 |
| 2017/0103498 A1* | 4/2017 | Waters | A61B 5/7217 |
| 2017/0148161 A1* | 5/2017 | Griffin | A61B 5/0084 |
| 2019/0029624 A1* | 1/2019 | Kunio | A61B 90/39 |
| 2019/0059734 A1* | 2/2019 | Yamada | A61B 5/0066 |
| 2019/0110776 A1* | 4/2019 | Yu | A61B 5/0035 |
| 2020/0086086 A1* | 3/2020 | Barone | A61M 25/0662 |
| 2020/0355557 A1 | 11/2020 | Friedman et al. | |
| 2021/0018408 A1* | 1/2021 | Dobosz | G01N 1/34 |
| 2021/0239451 A1* | 8/2021 | McMorrow | G01B 9/02091 |
| 2022/0040402 A1* | 2/2022 | Elmaanaoui | A61B 5/0073 |
| 2022/0044396 A1* | 2/2022 | Athanasiou | G06T 7/0012 |
| 2022/0218205 A1* | 7/2022 | Brushett | A61B 5/02007 |
| 2023/0184536 A1* | 6/2023 | McMorrow | A61B 5/0066 356/479 |

OTHER PUBLICATIONS

International Search Report and Written Opinion issued in Appln. No. PCT/US2022/018516 mailed Jun. 14, 2022 (12 pages).

* cited by examiner

SYSTEMS AND METHODS FOR AN AUTOMATIC PULLBACK TRIGGER

CROSS-REFERENCE TO RELATED APPLICATIONS

The present application claims the benefit of the filing date of U.S. Provisional Application No. 63/155,833, filed Mar. 3, 2021, the disclosure of which is hereby incorporated herein by reference.

FIELD

The disclosure relates generally to the field of vascular system imaging and data collection systems and methods. In particular, the disclosure relates to a system and methods for determining the existence of particular blood vessel conditions prior to initiating intravascular image capture over a length of the blood vessel.

BACKGROUND

Coronary artery disease is one of the leading causes of death worldwide. The ability to better diagnose, monitor, and treat coronary artery diseases can be of life saving importance. Intravascular optical coherence tomography (OCT) is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution. Viewing subsurface structures with high resolution using fiber-optic probes makes OCT especially useful for minimally invasive imaging of internal tissues and organs. This level of detail made possible with OCT allows a user to diagnose as well as monitor the progression of coronary artery disease.

OCT imaging of portions of a patient's body provides a useful diagnostic tool for doctors and others. For example, imaging of coronary arteries by intravascular OCT may reveal the location of a narrowing or stenosis. This information helps cardiologists to choose between an invasive coronary bypass surgery and a less invasive catheter-based procedure such as angioplasty or stent delivery.

OCT combines the principles of ultrasound with the imaging performance of a microscope and a form factor that is familiar to clinicians. Whereas ultrasound produces images from backscattered sound "echoes," OCT uses infrared light waves that reflect off the internal microstructure within the biological tissues. The frequencies and bandwidths of infrared light are orders of magnitude higher than medical ultrasound signals resulting in greatly increased image resolution; about 8-25 times greater than ultrasound or x-ray based modalities. OCT uses coherence-gating to detect singly-scattered photons thereby permitting tomographic imaging similar to ultrasound or computed tomography (X-ray), but at much higher resolution. While standard electronic techniques are adequate for processing ultrasonic echoes that travel at the speed of sound, interferometric techniques are required to extract the reflected optical signals from the light used in OCT. The output, measured by an interferometer, is computer processed to produce high-resolution, real-time, cross sectional or 3-dimensional images of the tissue. This powerful technology provides in situ images of tissues at near histological resolution without the need for excision or processing of the specimen.

A potential limitation of cardiovascular OCT is that it cannot produce clear images of a lumen wall when blood is present within the lumen, as the components of red blood cells strongly scatter the near-infrared light, making image reconstruction difficult. As a result, there is a need for systems and methods that facilitate detecting when blood has been cleared from a lumen. The aspects and embodiments of the invention discussed below addresses this need.

SUMMARY

The systems and methods of the present disclosure process intravascular image frames to identify, substantially in real-time, when blood has been sufficiently cleared from a blood vessel, so as to allow for the imaging of the blood vessel wall. The disclosed systems and methods allow for the identification of an initial blood clearing state, which corresponds to the instant when blood has begun to be cleared from the vessel. In addition, a final blood clearing state may be identified based on a determination that visibility within the vessel is no longer improving. The visibility within the blood vessel is determined based on the identification of edges within scanlines of a plurality of image frames captured consecutively or within a given period of time. As blood is removed, the identified edges within each image frame will have, on average, a larger offset from the center axis of the vessel lumen. The edges of a plurality of scanlines may be analyzed to determine an average edge offset for each image frame, and the average edge offsets for a plurality of image frames may be averaged over various time-windows, so as to determine when particular blood clearing states have occurred. The clearing of blood from the vessel may be divided into three states: 1) the "pre-clearing state" corresponds to the period of time in which there is typical amount of blood within the vessel; 2) the "currently-clearing state" corresponds to the period of time in which blood is in the process of being cleared from the vessel; and 3) the "sufficiently-cleared state" corresponds to the period of time in which blood has been sufficiently cleared from the vessel. The transition from the pre-clearing state to the currently-clearing state may be referred to as the moment of initial clearing, and the transition from the currently-clearing state to the sufficiently-cleared state may be referred to as the moment of final clearing. The vessel may also degrade back to a previous state, for example the vessel may degrade from the currently-clearing state to the pre-clearing state without ever reaching a sufficiently-cleared state. Once it has been identified that a vessel has reached the final clearing transition to enter the sufficiently-cleared state, the disclosed system may automatically initiate a catheter pullback procedure, so as to capture intravascular images over a length of the vessel that has been cleared of blood. Other features and advantages of the disclosed embodiments will be apparent from the following description and accompanying drawings.

Methods and systems of identifying blood clearing within the lumen of a vessel are disclosed herein. In accordance with aspects of the disclosure, one or more processors are configured to: acquire a plurality of intravascular image frames of a lumen; calculate an average edge offset for a plurality scanlines within the plurality of intravascular image frames; identify a first clearing event based the average edge offset for a first set of image frames increasing in accordance with one or more initial condition; identify a second clearing event based on the occurrence of the initial clearing event and based on the average edge offset of a second set of image frames having not increased in accordance with one or more final conditions; automatically initiating a catheter pullback procedure based on the identification of the final clearing event and based on identification that the lumen is in a sufficiently-cleared state.

In accordance with other aspects of the disclosure, the one or more initial conditions may comprise at least one of the following: 1) a short-term time-windowed average edge offset is larger than a predetermined maximum value; and 2) the short-term time-windowed average edge offset is greater than a baseline time-windowed average edge offset by at least a particular offset amount. In addition, the predetermined maximum value may set to be larger than a maximum catheter outer diameter offset. The particular offset amount may be, for example, 40 microns. The short-term time-windowed average edge offset may be calculated using a predetermined number of recently captured image frames. The baseline time-windowed average edge offset may be calculated using image frames captured over a period of time that is greater than 0.5 seconds.

In accordance with other aspects of the disclosure, the one or more final conditions may comprise at least one of the following: 1) a per-frame increment of an intermediate time-windowed average edge offset is less than a maximum per-frame increment of the intermediate time-windowed average edge offset for image frames captured after the initial clearing event; and 2) a predetermined period of time has passed since a largest clearing area has been observed in one or more of the plurality of image frames. The intermediate time-windowed average edge offset may be based on image frames captured over a period of time that is less than 0.5 seconds. The largest clearing area may be based on an average edge offset for one or more image frames and wherein the predetermined period of time is at least 40 seconds.

In still other aspects of the disclosure, the edge threshold may be computed based on identification of a minimum pixel intensity value and a maximum pixel intensity value over ranges of the scanlines for one or more image frames.

In yet other aspects of the disclosure, the plurality of intravascular images are captured by a catheter devices having a sheath with a clear layer and a doped layer, and wherein computing the edge threshold comprises identifying the minimum pixel intensity value within a scanline range corresponding to the clear layer and identifying the maximum pixel intensity value within a scanline range corresponding to the doped layer. The edges within the plurality of intravascular image frames may be based on identification of at least one pixel intensity value of a selected scanline having an intensity that is greater than a first edge threshold and based on identification of at least one pixel intensity value of the selected scanline having an intensity value less than a second edge threshold, wherein the first edge threshold is greater than the second edge threshold.

DETAILED DESCRIPTION

Figure 1:
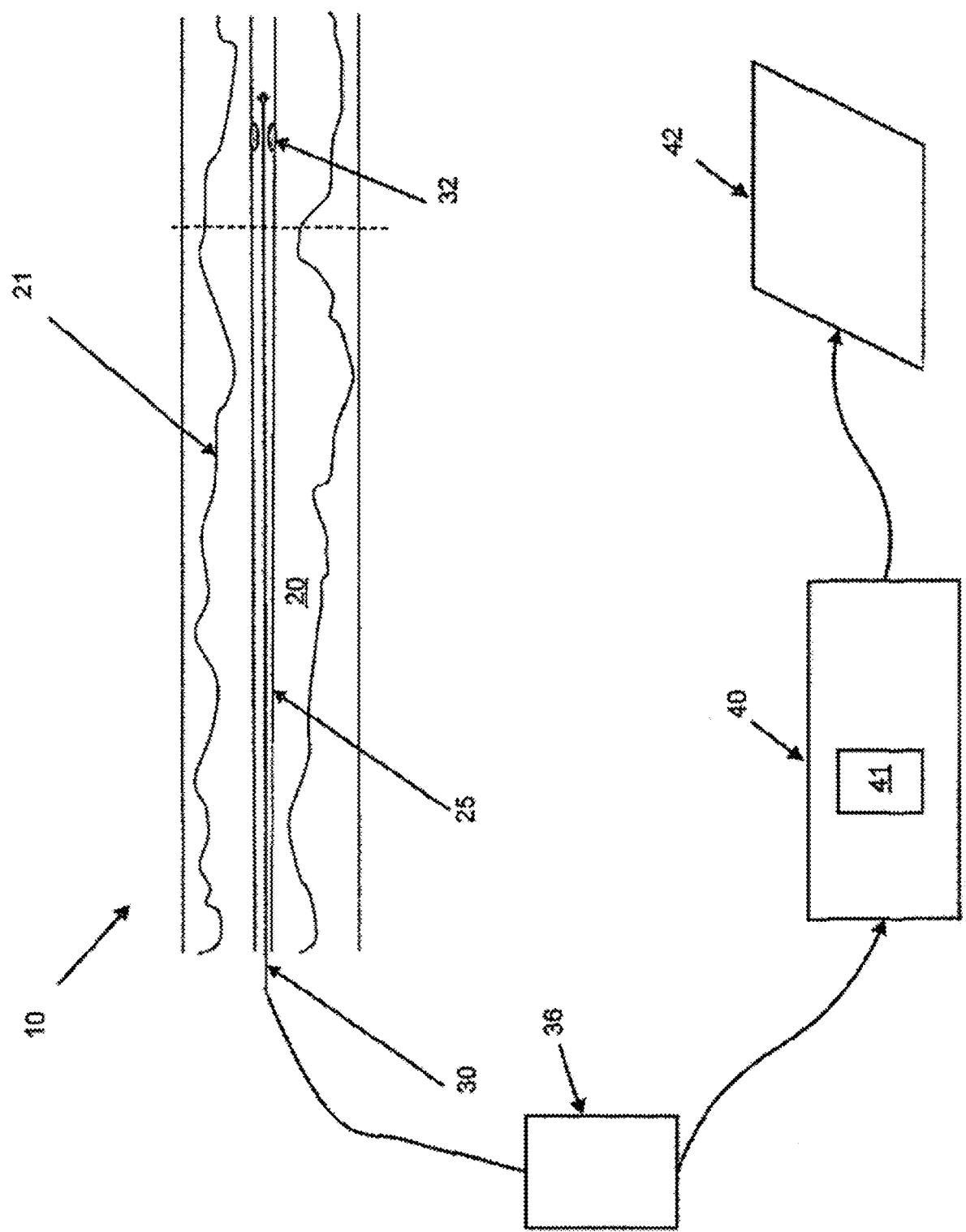
FIG. 1 is a schematic diagram of an OCT imaging and data collection system in accordance with aspects of the disclosure.

FIG. 1 is a schematic diagram depicting components of an OCT system 10. The OCT system 10 can include any suitable light source that satisfies the coherence and bandwidth requirements of the applications and data collection described herein. A vessel of interest 20 contains a vessel wall 21 defining a vessel lumen, which is imaged using catheter 25. A portion of catheter 25 has an optical fiber-based imaging probe 30 disposed therein. The catheter 25 may include a flushing subsystem having flush ports 32. The flushing system can be of any suitable type or variety that displaces a sufficient amount of blood such that in vivo OCT data collection can proceed using the probe 30. The system 10 includes an OCT system or subsystem 36 that connects to the imaging probe 30 via an optical fiber. The OCT system or subsystem 36 can include a light source such as a laser, an interferometer, various optical paths, a clock generator, photodiodes, and other OCT system components.

One or more computers or processors can be part of the OCT system 36 or can be included as a separate subsystem 40 in communication with the OCT system 36. The computers or processors 40 can include memory, storage, buses and other components suitable for processing data and executing a flush process or a software triggering method for lumen detection and pullback data collection as discussed below. In one embodiment, the computer or processor includes software implementations or programs 41 of the methods described herein that are stored in memory and executed using a processor. A display 42 can also be part of the overall system 10 for showing cross-sectional scan data as longitudinal scans or in other suitable formats.

A limitation of cardiovascular OCT is that it cannot capture clear lumen images through blood, due to the scattering of the near-infrared light by blood cells. Thus, suitable image reconstruction of the lumen wall 21 is not possible when OCT images are captured prior to blood being cleared from vessel 20. Accordingly, in order to capture OCT images of the lumen wall 21, the vessel 20 is temporarily cleared of blood for a period of time. Displacing the blood via a flush solution such as saline applied through the port 32 is possible, but the flush rate must be sufficient to overcome the native flow, which in coronary arteries is relatively high, 1-5 ml per second. About 3-5 seconds of clear image time can be established with flush-based approaches.

The amount of clearing time that can be established for a typical bolus (10-20 ml), is dependent on many factors such as the local blood flow rate, arterial size/imaging location, prevalence of side-branches, etc. However, it is typically in the range of about 2 to about 5 seconds. The amount of time to acquire an OCT pullback recording (OCT data collection process) is in the range of about 2 to about 4 seconds. Accordingly, it is desirable that the OCT data acquisition during the pullback is initiated the moment sufficient clearing has been established.

It is desirable for a computer-based method to process the scanned images in substantially real-time (or other OCT system specified time period suitable for a given application) and trigger the pullback when sufficient clearing has been detected. The computer system 40 can execute the methods described herein. In one embodiment, the methods and system described herein may analyze at least 180 frames/sec of complex image data in real-time, and use the analyzed OCT frames to identify when the blood vessel is in a state of sufficient clearing, so that pullback can be initiated.

It is important for a system to be able to correctly determine the moment at which the vessel has been sufficiently cleared of blood, and a physician may consider even a 400 millisecond delay in identifying a sufficiently-cleared state as undesirable. By minimizing the delay in beginning image acquisition, the current system can make the best use of the flush medium injected into the body, can maximize the cleared portion of the pullback, can minimizing the presence of blood re-entering vessel at distal end of the pullback, and can maximize the utility of the recording to provide information on optimal treatment of the vessel. Alternatively, a false positive determination of a cleared state can cause the OCT pullback procedure to commence prior to the vessel being cleared of blood. Thus, the disclosed systems and methods herein are directed toward the accurate identification of a cleared state, thereby preventing the OCT pullback from occurring either too early or too late. Suitable methods of detecting the flush clearing on a reliable and real-time basis using an automated software-based system or method is one feature of this invention.

The currently disclosed systems and methods are also designed to work in a wide variety of environments, including in environments where the exact shape and size of the lumen is unknown. In addition, the disclosed systems and methods allow for detection of blood clearing for small lumens, such as those with a diameter of approximately two millimeters. Other blood clearing detection methods are often unable to identify a cleared state for such small lumens, as they require a certain degree of change in the detected lumen wall offset in order to establish that the lumen has been cleared.

Software detection of vessel lumen flush clearing is performed as outlined below such as using all or a subset of the methods described below. Once a suitable clearing state is achieved the software automatically triggers the acquisition of an OCT intravascular pullback data collection process or recording. The software-based method may be used to detect the clearing status of the artery. This software-based method processes OCT images of the artery in substantially real-time to determine a clearing radius metric and quality metric value for each image. When the clearing radius and other potential quality metric values meet the predefined "fully-clear artery" criteria then the pullback and data acquisition may automatically start. Pullback refers to when the probe 30 and/or catheter 25 is pulled back through a vessel 20 to collect data for use in assessment and treatment of the vessel. As the probe 30 and/or catheter 25 is pulled back OCT data is collected and sent to the OCT system 36 and/or the computer system 40. When the probe 30 is longitudinally stationary, data is sent to the computer system to execute a clear state detection method following initialization of a flush.

With respect to FIG. 1, if the vessel of interest 20 is a coronary artery, OCT imaging of the coronary artery may be performed using an OCT fiber optic imaging catheter such as catheter 25 with probe 30. The OCT imaging catheter 25 is placed in the artery at the location where a pullback recording is to be started and the OCT software computer-based method flush clearing detection is initialized (enabled). The operator of the OCT system will then inject a clearing medium (flush) such as (saline, contrast solution, dextran or equivalents) into the artery to clear it for imaging. The flush clearing detection method executing on the computer 40 will then determine when the injected flush has provided sufficient clearing in the artery to allow the OCT system to acquire a good image. The pullback will be triggered by the computer when such a determination has been made. The determination of sufficient clearing may be made in real-time by processing each frame as it is acquired by the OCT system 36 or computer system 40.

The system shown in FIG. 1 may be configured to process each captured OCT image frame within vessel 20. In processing each image frame, the image may be analyzed to identify edges or boundaries within the image and to determine the amount of offset of the identified edges from the center of the lumen. When blood is present within vessel 20 light from the imaging catheter 25 will be scattered by the blood cells, so that any identified edge will have a small offset from the center axis along the radial axis. As blood is cleared from vessel 20, the identified edge within the OCT images will have a greater offset from the catheter's center axis.

Figure 2:
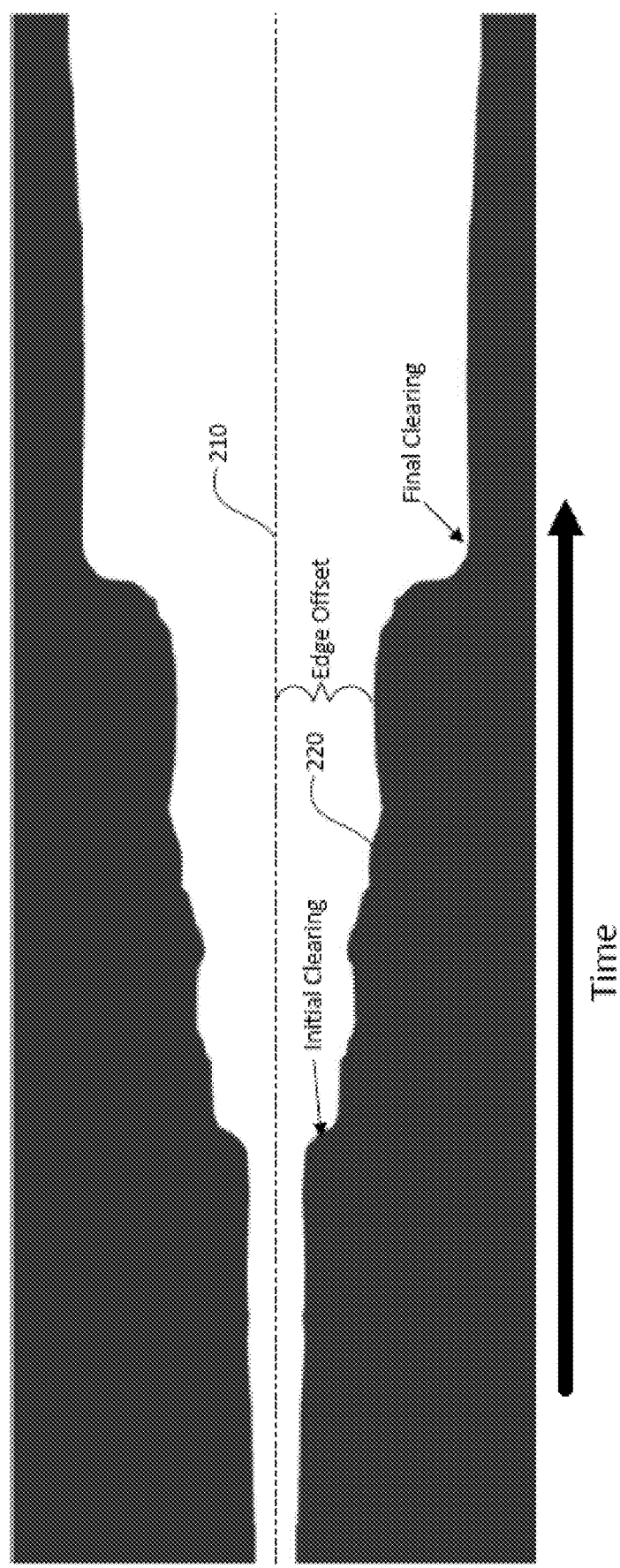
FIG. 2 is a pictorial representation of observed blood clearing within a lumen in accordance with aspects of the disclosure.

FIG. 2 is a pictorial representation of the edge offset that is observed at a particular location within a vessel over a period of time, as blood is being cleared from the vessel. The dashed line 210 of FIG. 2 represents the center axis of the imaging catheter, while the boundaries 220 of the dark regions represent the observed edge that is identified by analyzing light from the OCT catheter, as it captures intravascular image frames over a period of time. The distance between the dashed line 210 and the boundary 220 represents the average edge offset that is observed at a given moment in time. As can be seen in FIG. 2, the edge offset is initially relatively small. This is due to the presence of blood within the lumen. As blood is cleared from the lumen, the boundary 220 of the observed edge moves farther from the vessel's center axis 210. In accordance with the current disclosure, the point at which the edge offset begins to widen is identified as the moment of initial clearing. Once an initial clearing has been observed, the vessel is in a currently-clearing state and the disclosed system may then determine if the vessel has entered a sufficiently-cleared state or has regressed back to a pre-clearing state. In FIG. 2, the vessel experiences a "final clearing," so as to transition from a currently-clearing state to a sufficiently-cleared state. As set forth below, the sufficiently-cleared state may be based on a determination that the average edge offset reaching a relatively cleared and stable state over a predetermined period of time. Upon identifying that the vessel has experienced a final clearing, so as to enter a sufficiently-cleared state, the system described above in connection with FIG. 1 may be configured to automatically initiate the pullback procedure in which the catheter is pulled along a predetermined length of the vessel and OCT images are captured over that length. Since the vessel has been cleared of blood during the pullback procedure, the captured OCT images will be minimally obscured by blood within the vessel.

Figure 3:
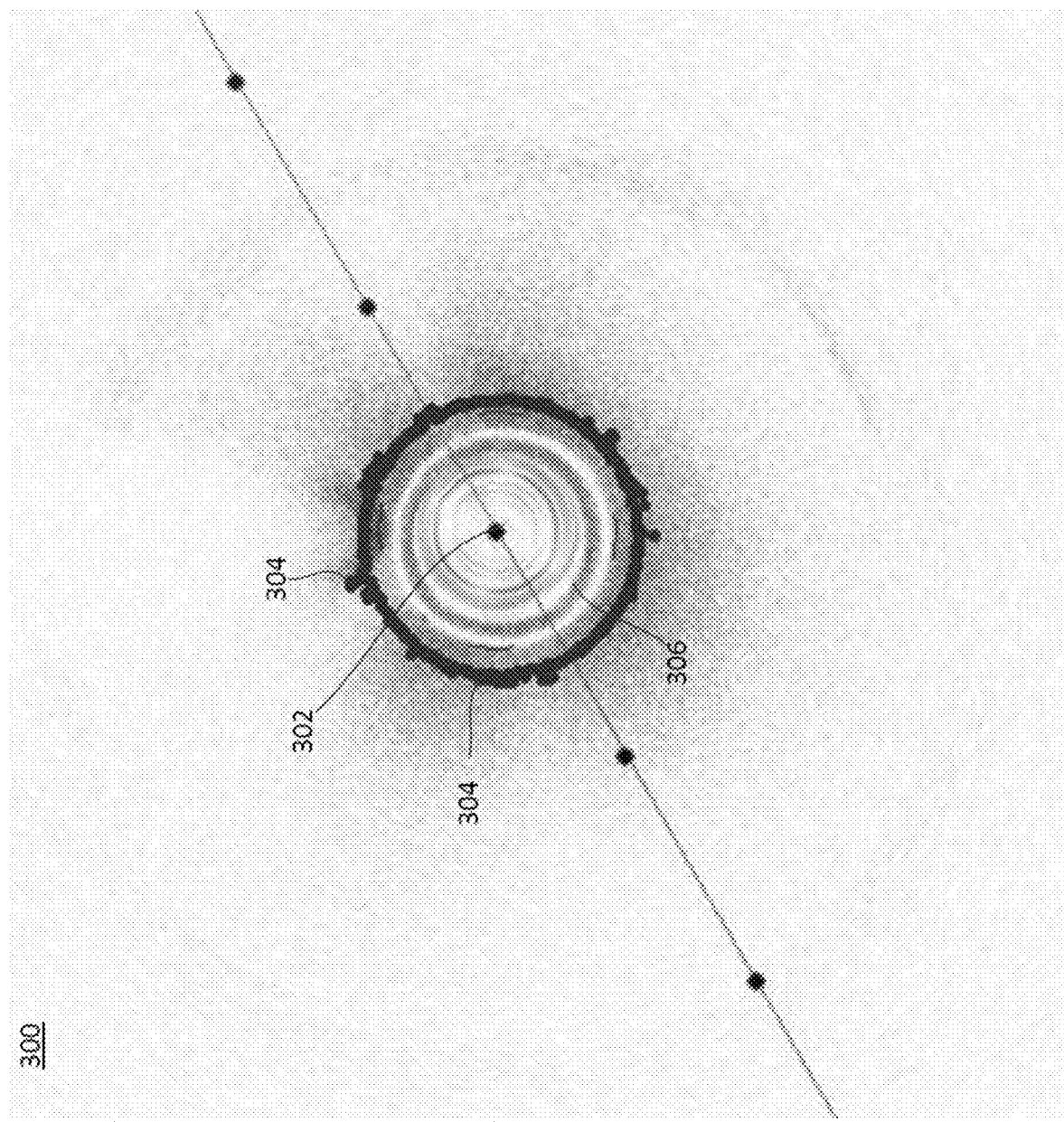
FIGS. 3-5 are annotated OCT image frames representing different periods during the blood clearing process in accordance with aspects of the disclosure.
Figure 4:
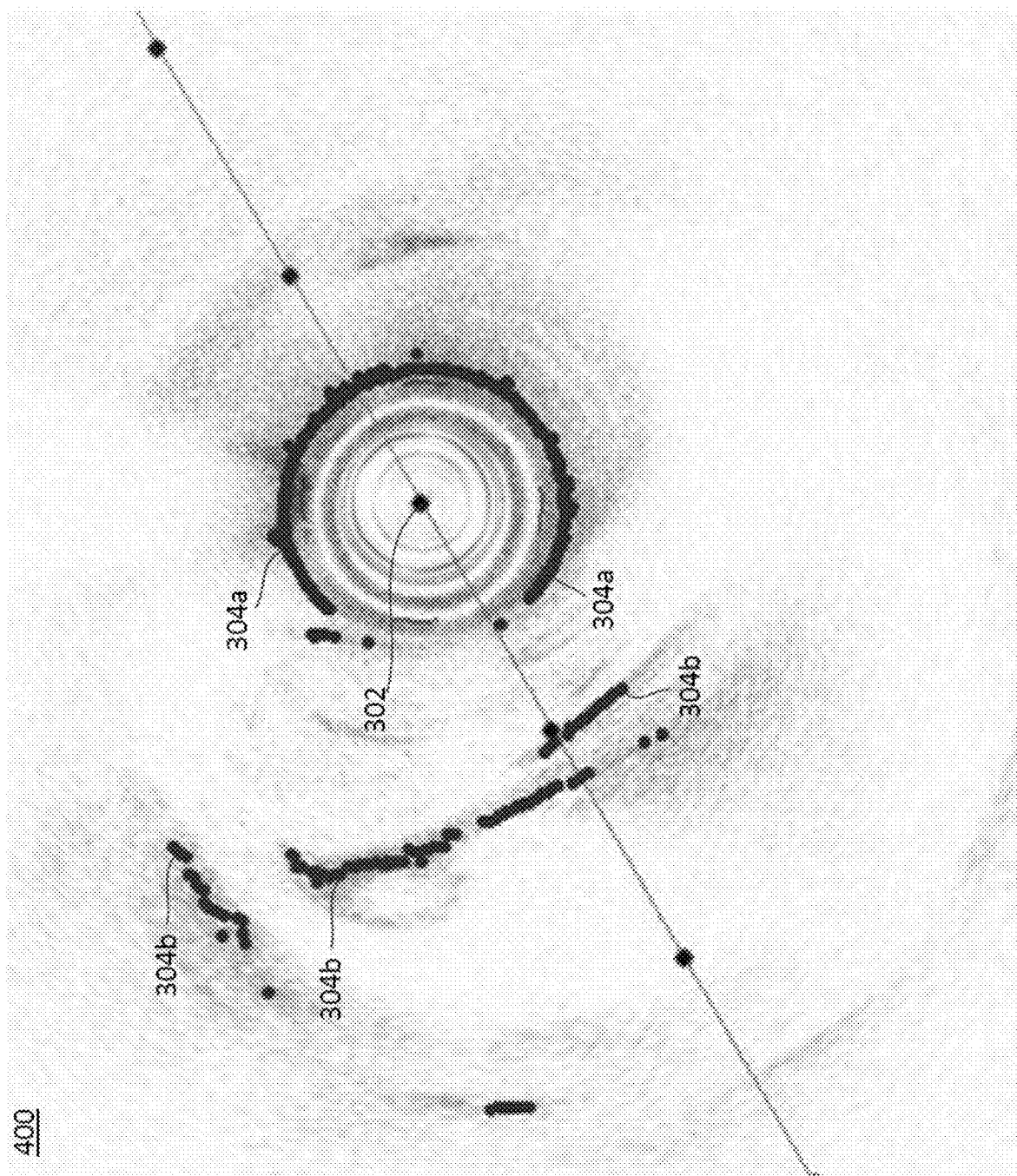
Figure 5:
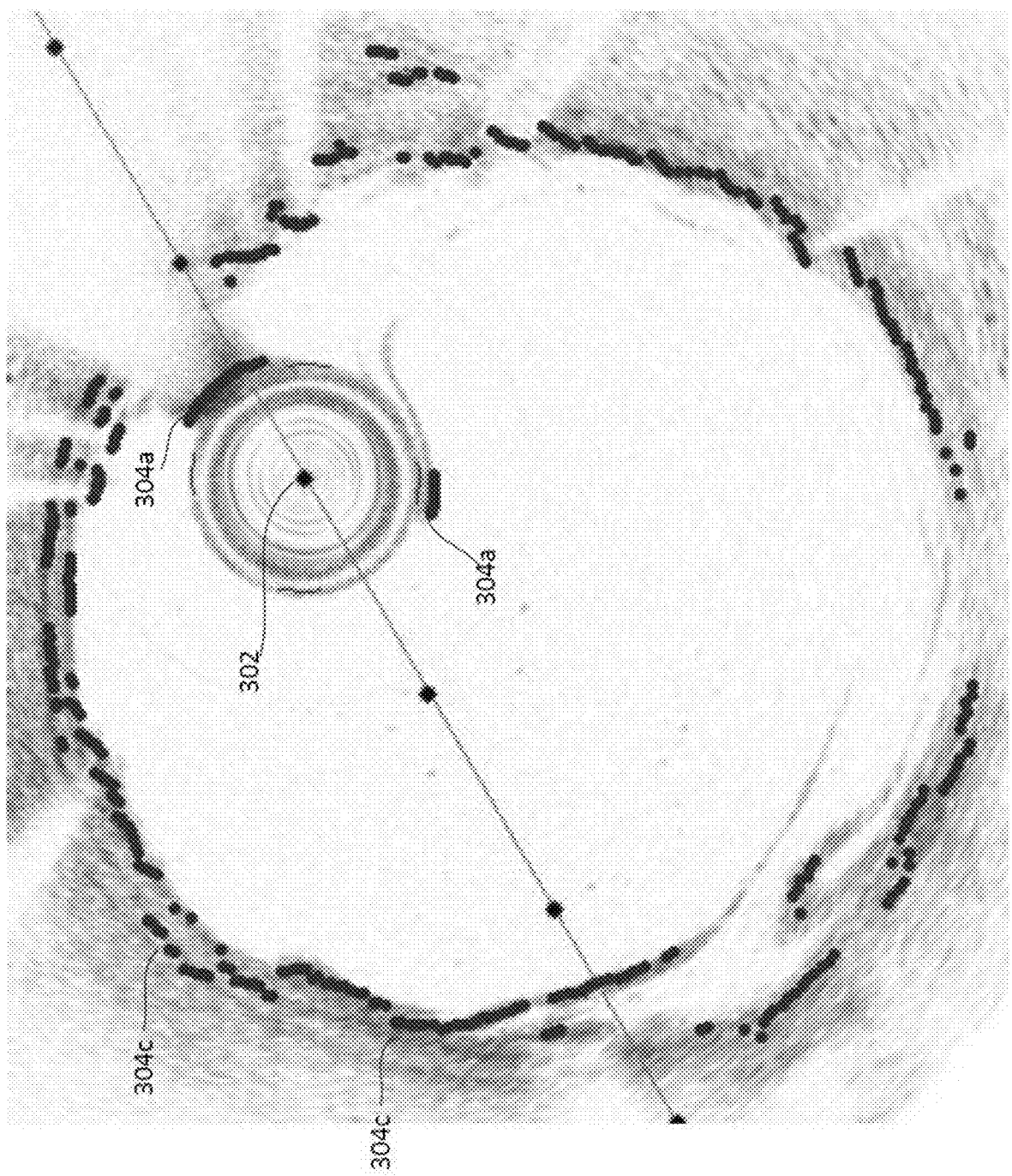

In accordance with aspects of the current disclosure, the system of FIG. 1 may process captured OCT image frames so as to calculate the average edge offset ("AEO") of each image frame. FIGS. 3-5 are examples of three annotated OCT image frames that can be captured at a particular location within the vessel of a patient's artery by catheter-based data collection probe 30 of FIG. 1. FIG. 3 is of OCT image frame 300 where blood has not been cleared from the vessel. In processing OCT image frame 300, each scanline of the image may be analyzed to identify an edge offset from the center 302 of the catheter. The OCT image may be analyzed in polar coordinates so that each scanline is processed as an A-line relative to the center 302 of the catheter. Each annotation point 304 represents an observed edge for each scanline. For clarity, only two of the annotation points 304 have been given reference numbers in image 300. As shown in image 300, the identified points 304 form a circle around the center 302, with the points 304 each being a similar distance from center 302. The distance of each point 304 from center 302 may be calculated and stored as an "edge offset." This distance may be based on the number of image pixels between a point 304 and center 302. The image is represented in 2-D Scan converted coordinates so it has a representation that physically looks like the catheter and the blood field. However, the offset measurements are typically performed radially in polar coordinates, and all image processing may be performed in such polar coordinates. Based on the edge offset of each point 304, an average edge offset may be calculated, representing the average distance from center 302 for the identified edges for all scan lines within the image frame. The observed ring 306 around the center 302 is the result of the catheter sheath having doped and clear layers, which produce differing levels of pixel intensity. As set forth below, the disclosed systems and methods may use edge detection processes that account for these doped and clear layers of the catheter sheath. The doped and clear layers of the catheter sheath can be used to identify the outer edge of catheter sheath, and the search for the image edges may be configured to proceed radially outward starting from just beyond the outer edge of the catheter sheath. By starting just beyond the outer edge of the catheter sheath, the system will avoid having an edge being identified at any thin layer of blood that remains attached to the sheath of the catheter. In addition, the doped and clear layers of the catheter sheath may be used to sample image pixel intensities, so as to identify a suitable threshold value for the edge detection within the image.

FIG. 4 is OCT image frame 400, which has been captured at a period of time in which contrast solution begins to flush the vessel, so as to clear blood from the vessel. Some the observed edges for some of the scanlines remain the same distance from center 302 as the edges identified in image 300 of FIG. 4. Some of these edges are identified in image 400 as annotation points 304a. However, the edges for some scanlines in image 400 now have a larger offset from center 302, as can be seen for annotation points 304b. Given the increased edge offset for some scanlines, the average edge offset for image 400 will be larger than the average edge offset of image 300. This increase in the average edge offset of image 400 relative to image 300 may be used to determine that the vessel has experienced initial clearing, as the vessel has transitioned from the pre-clearing state to a currently-clearing state, as discussed above in connection with FIG. 2.

FIG. 5 is an OCT image frame 500 that has been captured at a period of time in which contrast solution has continued to flush the vessel, so as to continue to clear blood from the vessel. As can be seen in FIG. 5, image frame 500 contains a large number of scanlines in which the edge offset is larger than the edge offset shown in either image frame 300 or 400. In particular, annotation points 304c represent scanlines in which the observed edge corresponds to the vessel wall. Thus, the edge offset for these scanlines will not significantly increase any further, even as blood is continued to be flushed from the vessel. Annotation points 304a represent scanlines in which blood or another substance is still causing backscatter relatively close to center 302. However, the scanlines containing annotation points 304a are relatively small in number (less than 20%) compared to the scanlines containing annotation points 304c. Thus, the average edge offset for image frame 500 will have begun to approach a relatively stable value, as most of the edge offsets will no longer be significantly changing from one image frame to the next. In accordance with aspects of the disclosure, the vessel can be determined to have transitioned from a currently-clearing state to a sufficiently-cleared state based on the calculated average edge offset being relatively stable over a series of OCT image frames.

Figure 6:
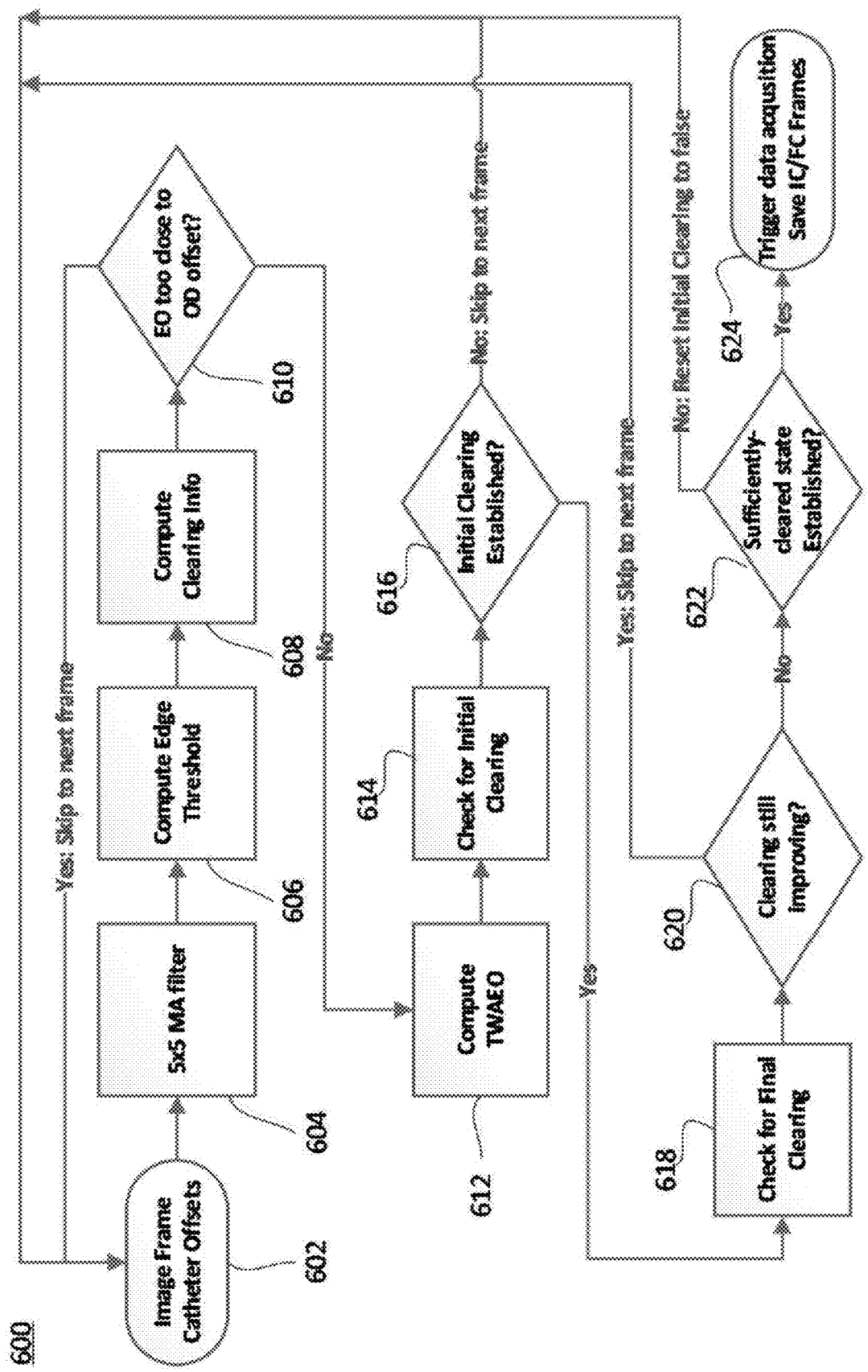
FIG. 6 is a flow diagram for identifying an initial clearing state and a final clearing state in accordance with aspects of the disclosure.
Figure 7:
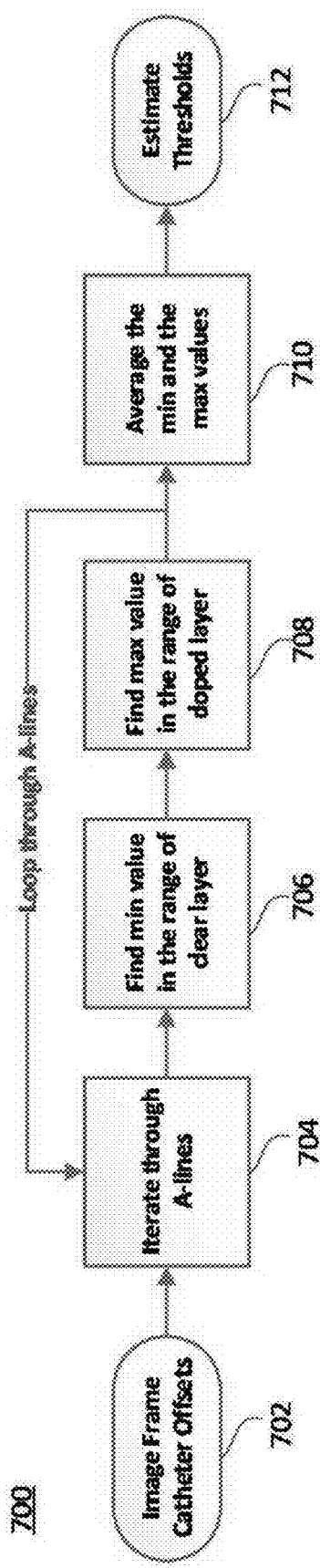
FIG. 7 is a flow diagram for computing edge thresholds in accordance with aspects of the disclosure.
Figure 8:
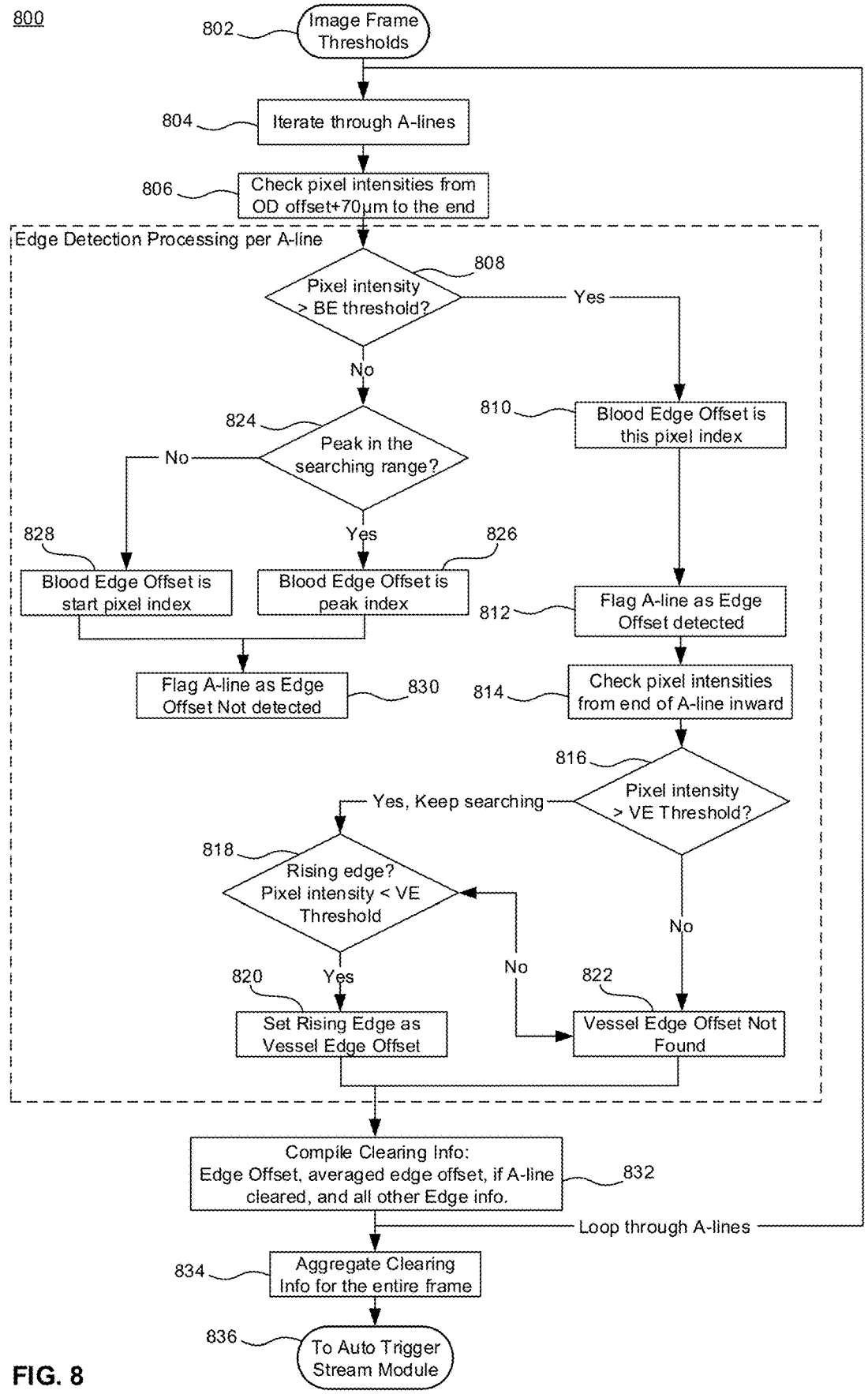
FIG. 8 is a flow diagram for computing blood clearing information in accordance with aspects of the disclosure.

FIGS. 6-8 are flow diagrams that provide an example by which the system shown in FIG. 1 may identify an initial clearing and a final clearing of a vessel in accordance with the current disclosure. While the operational blocks of FIGS. 6-8 are each provided in a particular order, one or more processors of the disclosed system may be configured to add operations, remove operations, or switch the order of the operations in accordance with aspects of the method and system.

FIG. 6 is flow diagram 600 for which OCT image frames are used to identify that a vessel has experienced an initial clearing and a final clearing. The OCT images may be processed frame by frame from a live image pipeline, with image frame and catheter offset data provided as inputs at Block 602. At Block 604, the image data may be smoothed to reduce noise. This smoothing may be accomplished using a filter kernel, such as 5×5 spatial moving average box-car filter kernel. At Block 606, edge thresholds are computed for the image data so that the edge offset and related blood clearing information may be compiled in Block 608. Examples of processes for computing the edge thresholds (Block 606) and blood clearing information (Block 608) are provided in FIGS. 7 and 8, respectively. As previously discussed above, the application of the edge thresholds to an image frame may include identification of an edge at each scanline, and the offset of each identified edge from the center of the vessel will be computed as an edge offset, which represents blood clearing information. The edge offsets for each scanline of the image frame may be used to compute a single average edge offset of each image frame. This average edge offset may be the mean value of the edge offsets or it may be the result of another form of statistical analysis of the plurality of edge offsets.

At Block 610, a check may be performed to determine if too many edge offsets are within a predefined distance from the catheter's outer diameter offsets. For example, it may be determined whether the edge offsets are within 120 microns from the catheters outer diameter offset, and if a certain percentage, such as 80%, of the edge offsets are within this predefined distance, then the system will skip the current image frame and proceed to processing the next image frame in the live pipeline. If the edge offsets of the image frame are not too close to the outer diameter offset of the catheter, the system may proceed to process the image frame by computing time-windowed average edge offsets (TWAEOs), as provided at Block 612. A TWAEO represents a time-windowed average of all average edge offsets that have been calculated over a particular time period or over a particular number of image frames. In particular, the system may compute multiple TWAEOs based on windows having different time periods or having a different number of image frames. For example, a baseline time-windowed average edge offset, TWAEO1, may be calculated by taking a time-windowed average of the average edge offsets for image frames that have been captured over the last 1 second, or for some other time period that is sufficiently large to establish a baseline. The baseline time-window will typically need to be at least 0.5 seconds or greater in order to establish a long-term average edge offset. An intermediate time-windowed average, TWAEO2, may be based on taking average of the average edge offsets that have been calculated for image frames captured over time-window of less than 0.5 seconds. For example the intermediate time-window may be 0.2 seconds. In addition, a short-term time-window average, TWAEO3, may be calculated based on a fixed number of recently-captured frames. For example, TWAEO3 may be the time-window average of the average edge offsets for the last four image frames in the pipeline.

TWAEO1 may be used to represent a baseline time-window, as it is based on the average edge offsets for a large number of image frames that have been captured over a relatively long time horizon. The number of image frames that are included in this 1-second window of time will be based on the frame rate of the OCT imaging device, but for some OCT imaging devices, a 1-second window will include around 180 image frames, representing 180 frames per second high speed spin. Regarding TWAEO2, this time-window average may be used to check the edge offset increment, so as to assess clearing improvement trends and to determine if a final clearing has occurred. The short-term window of TWAEO3 may be used to identify instant edge offset changes, as they occur over a predetermined plurality of image frames.

One or more TWAEOs that are calculated at Block 612 may be used at Block 614 to determine if the vessel has entered an initial clearing state. As previously discussed, the initial clearing is one in which blood has begun to be cleared from the vessel, so the vessel may be considered to have transitioned from a pre-clearing state to a currently-clearing state. The initial clearing can be identified based on an increase in the average edge offset that is observed in the image frames. The determination of an initial clearing can be based on one or more of the calculated TWAEOs and may be based on determining that at least one of multiple initial conditions have been met. A first condition may be based on an absolute amount of average edge offset that is consistent with the vessel experiencing an initial clearing of blood, while a second condition may represent a short-window increase in the average edge offset relative to a longer time-window baseline. For example at Block 614, it may be determined whether the vessel has experienced an initial clearing if either of the following conditions are met: 1) TWAEO3 is larger than 120 microns beyond the maximum value of the catheter outer diameter offsets for all A-lines in the image frame; or 2) TWAEO3 has increased more than 40 microns over the baseline offset of TWAEO1. The 120 microns and 40 micron values used for the first and second conditions are merely examples, and different values may be used based on the construction of the OCT catheter and catheter sheath. For example, the first condition could be modified so that it is satisfied for any TWAEO3 value that is larger than the catheter outer diameter offsets, and the second condition could be modified to be based on any increase in TWAEO3 relative to TWAEO1, provided that the increase is sufficient to indicate an actual increase in the average edge offsets.

If an initial clearing has not yet been identified, the vessel remains in a pre-clearing state, and the system may return to Block 602, where the next image frame in the pipeline is processed. If an initial clearing has been detected, the system may proceed to Blocks 618, where a determination is made if the vessel has experienced a final clearing, so as to transition from a currently-clearing state to a sufficiently-cleared state. The determination of a final clearing event can be based on one or more of the calculated TWAEOs indicating that the average edge offsets have reached a stable condition over a predetermined period of time, and this determination may be based on one or more final conditions having been met. A stable state of the average edge offsets may be identified when it is determined that the average edge offsets are no longer improving by some predetermined value or rate. For example, a determination may be made that the vessel has experienced "no-improvement" if either of the following two conditions are found to be met: 1) The per-frame based TWAEO2 increment is less than the maximum increment recorded during the processing of previous image frames by a predetermined amount, or 2) it has been more than a pre-determined period of time since the largest clearing area has been recorded. For example, in connection with the first condition, it may be determined that the blood clearing has entered a stable state when the per-frame based TWAEO2 increment is less than one-third of the maximum increment recorded during the processing of previous image frames. Other comparisons of time-windowed average edge offset may be used, provided that the comparison indicates that the increase in the average edge offsets have sufficiently slowed so as to indicate that the blood clearing has entered a final, stable state. For the second condition, the predetermined period of time may be, for example, at least 40 milliseconds, so that a final clearing is identified if the largest average edge offset of one or more image frames has been recorded more than 40 milliseconds ago. In addition, the predetermined period of time may be finely tuned, so as to start the pullback procedure as soon as the final clearing has been reached, but without causing a false positive identification of the final clearing. For example, the predetermined period of time for may be selected to be 44.44 milliseconds.

If a determination is made at Block 620 that the "no-improvement" conditions have not been met, then the system may return to Block 602 by proceeding to process the next image frame in the pipeline. However, if at least one of the "no-improvement" conditions have been met (Block 620), the system may determine if the vessel is in the sufficiently-cleared state (Block 622). This determination may be based on whether the cleared area of the currently processed image frame, or set of recently captured image frames, is larger than the initial clearing area. For example, the average edge offset of the current image frame may be compared against the average edge offset that was observed at or shortly after the occurrence of the initial clearing. If the current clearing area is sufficiently larger than the initial clearing area, then the vessel may be determined to have experienced a final clearing, so as to be in a sufficiently-cleared state. In particular, it may be determined whether the current clearing area is greater than or equal to initial clearing area multiplied by some value "K", where the value K is greater than or equal to 1.0. This K value may be adjusted to tune the sensitivity of the final clearing detection, so as to identify an instance in which blood has returned to the vessel. The larger the K value is, the higher the bar is for determining that final clearing has been reached. The system may then be configured to automatically initiate the pullback procedure, at which time the catheter is pulled through a predetermined length of the vessel while capturing images of the vessel wall. The images captured during the pullback may be saved and processed for diagnosis of the vessel. If a sufficiently-cleared state is not found to exist at Block 622, then the initial clearing state may be reset to false, and the system may return to Block 602 in order to process the next image frame in the pipeline.

FIG. 7 is a flow diagram 700 that provides an example of an edge threshold computation that can be performed in connection with Block 606 of FIG. 6. At Block 702, the smoothed image frame and catheter offset data are received. In computing the edge threshold, the system may use information relating to the detectable layers of OCT images that represent different layers of the catheter sheath. In particular, the catheter sheath may include a doped layer that corresponds to a region around the center of the OCT image, as well as a clear layer surrounding the doped layer.

Figure 9:
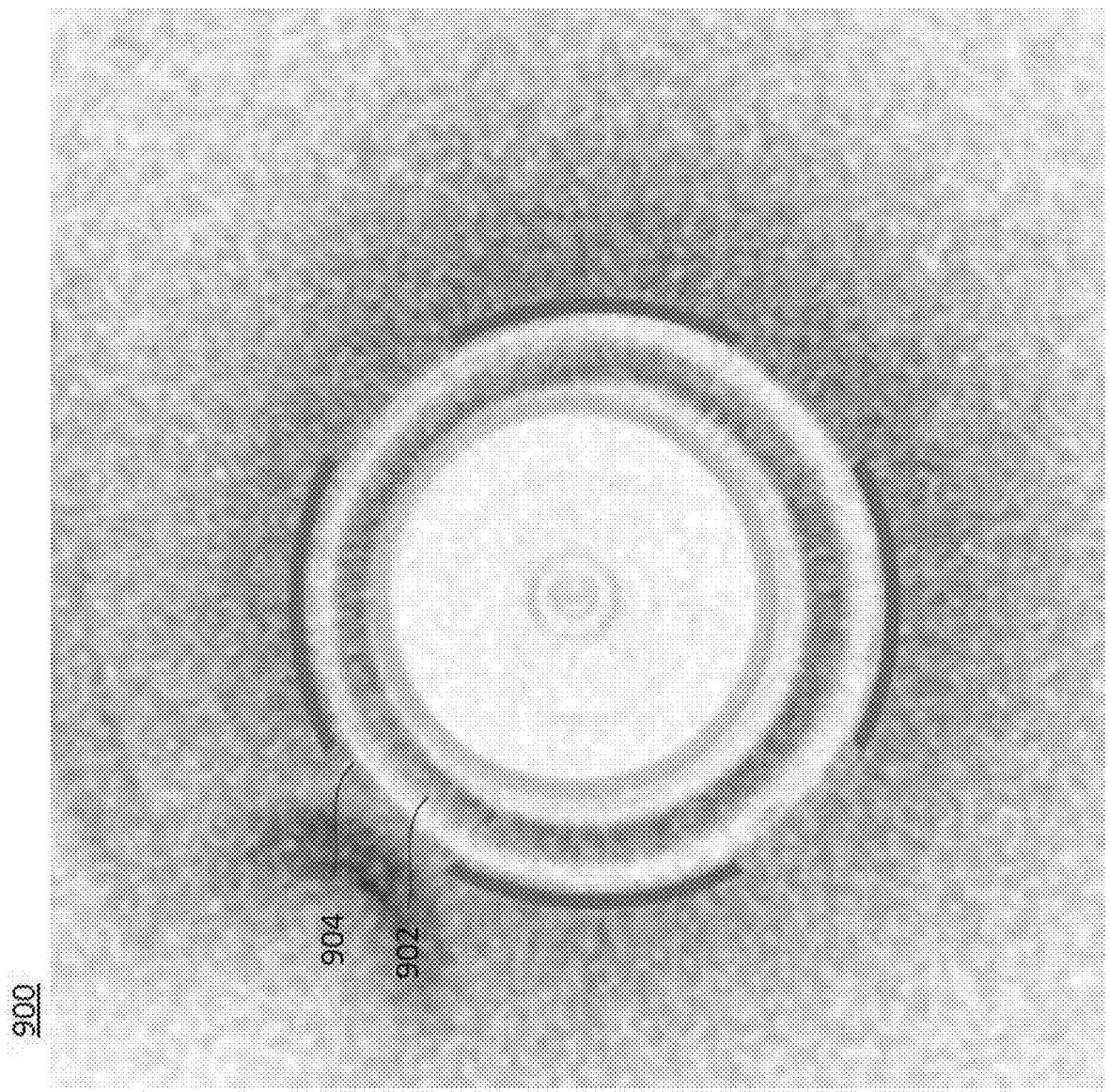
FIG. 9 is an OCT image frame in accordance with aspects of the disclosure.

Turning to FIG. 9, the doped layer and clear layer can be seen in OCT image 900. In particular, the doped layer of the catheter sheath can be identified by ring 902 that appears within image 900. Outside of ring 902, a ring 904 can be seen. This ring 904 corresponds to the clear layer of the catheter sheath. As set forth below, the doped layer and clear layer may be used to calibrate the threshold levels for identifying edges within the OCT image.

The doped layer may be a $TiO_2$ filled scattering layer. Image 900 is a negative of an OCT image, accordingly the doped layer appears as a dark ring, however in a standard image, the doped layer would appear as a bright band within the OCT image. The outer diameter layer is the outmost boundary of the imaging catheter. The catheter sheath offsets may be calculated by an OPTIS catheter sheath detection algorithm. For the edge threshold computation, the offsets for the doped layer and the outer diameter of the catheter sheath may be used.

Turning back to FIG. 7, at Block 704, the system iterates to another scanline/A-line in the image frame. At Block 706, the minimum/valley intensity value "$I_{min}$" in catheter clear layer is identified. At Block 708, the maximum/peak value "$I_{max}$" is identified for the doped layer, with the range for this maximum being between the doped layer inner boundary and the doped layer outer boundary. For example, for some catheter sheaths, the inner boundary location may be identified as approximately 0.0015 inch or approximately 38 microns inward from doped layer outer boundary, with a range from doped layer outer boundary to the outer diameter layer boundary. The iteration process of blocks 704 to 708 is then repeated through all scanlines of the OCT image frame.

At Block 710, an average of the $I_{min}$ and $I_{max}$ values may be calculated, and the threshold "$T_{tissue}$" may then be estimated based on the average of the $I_{min}$ and $I_{max}$ values (Block 712). For example, the threshold $T_{tissue}$ may be estimated based on the following equation:

$$T_{tissue} = \frac{\langle \sum_{\alpha=1}^{N} I_{min}(\alpha) \rangle}{N} + 0.8 * \left( \frac{\langle \sum_{\alpha=1}^{N} I_{max}(\alpha) \rangle}{N} - \frac{\langle \sum_{\alpha=1}^{N} I_{min}(\alpha) \rangle}{N} \right)$$

The summations set forth above occur over all of the scanlines of an image, starting from a first scanline "α=1" to a final scanline "N." This threshold value may then be used to identify edges within the image frame and compute clearing information at Block 608 of FIG. 6.

FIG. 8 is a flow diagram 800 that provides an example by which clearing information may be computed in connection with Block 608 of FIG. 6. The clearing information is based on the vessel's lumen and blood edge offsets that are observed in the image frame. In connection with Block 608 of FIG. 6, an edge detection algorithm may be applied as a 1-D edge finding kernel along each scanline of the image's polar coordinates, so as to detect rising edges and falling edges relative to the catheter sheath offset inputs. The searching range for edges may be of a predetermined distance from the outer diameter offset of the catheter sheath to the end of each A-line. In particular, the edge searching range may be set by a controllable variable that may be set to a value sufficient to avoid identifying a remaining thin wisp of blood. For example, the edge searching range may be set so that it is from 70 microns outward from the outer diameter offset to the end of each A-line. This 70-micron offset may be added to avoid the blooming that can occur at the edge of the outer diameter layer of the catheter sheath and to avoid small residuals of blood that may be hugging the catheter sheath. The edge detection algorithm may be configured to identify rising and falling edges with the threshold value computed in connection with flow diagram 700. In particular, $T_{tissue}$ may be used as the Blood Edge ("BE") Threshold and Vessel Edge ("VE") Threshold may be defined as a fraction, such as a half, of $T_{tissue}$.

An example of computing this clearing information data is provided in flow diagram 800 of FIG. 8. At Block 802 of flow diagram 800, the smoothed image frame and computed edge threshold data is accessed. At Block 804, the system iterates to the next A-line of the image frame to be analyzed. The system may then scan the pixel intensities from a location that is 70 microns from the outer diameter offset to the end of the selected A-line (Block 806) and then proceed to edge detection processing for the selected A-line.

Based on the defined VE Threshold and BE Threshold, the scanline may be processed to determine an edge offset for the scanline. As part of this determination, the algorithm may attempt to compute an offset to any blood that is present and an offset to the vessel edge. If both computations are successful, the computation may resolve to roughly the same offset, but in cases where there is blood but some clearing behind the blood, the computation will not resolve to the same offset. The determination of these offsets is further described below. When both a Blood and Vessel Edge offset are found, a search may be performed between the two offsets to determine if there is clearing, which may be indicated by the average intensity between offsets being less than a clearing threshold. Such a clearing threshold may be the Blood Edge Threshold divided by 3.3. If this condition is satisfied, this indicates substantial clearing between the two offsets, and the farther of the offsets (the Vessel Edge offset) is chosen as the scanline's edge offset. Otherwise the Blood Edge offset is chosen as the edge offset.

For example, at Block 808, by searching from the catheter outward, a determination is made whether a pixel intensity in the selected A-line is greater than the Blood Edge Threshold. If a pixel sample does have an intensity greater than the BE Threshold, then a Blood Edge offset is identified at the index of the first pixel with intensity greater than the threshold (Block 810), and the A-line is flagged as having a detected edge offset (Block 812). At block 814, pixel intensities may be checked from the end of the A-line inward, towards the center of the vessel, and a determination is made whether a pixel intensity is greater than the VE Threshold (Block 816). If a pixel intensity is greater than the VE Threshold, a search of the A-line continues to find the first pixel, after the sample greater than VE Threshold, whose intensity is less than VE Threshold, so as to indicate the existence of a rising edge (Block 818). If Block 818 determines the existence of a rising edge, the rising edge is set as the vessel wall edge offset (Block 820). If the determinations for either Block 816 or Block 818 are not satisfied, then it is determined that a vessel wall edge offset is not found (Block 822).

Returning to Block 808, if the pixel intensities along the A-line are not greater than the BE Threshold, then a determination is made whether a peak exists in the searching range (Block 824). If so, the blood edge offset is associated with the index location of the peak (Block 826). If Block 824 does not identify a peak in the searching range, the blood edge offset is associated with the start of the pixel index (Block 828). At Block 830, the A-line is flagged as no vessel wall edge offset having been detected.

The resulting edge offsets of each scanline/A-line may be used in the computation of the average edge offset for the image frame. At Block 832, the clearing information is compiled, including edge offset, averaged edge offset, identification of whether the A-line is cleared, and all other edge information. The system may then return to Block 804, so as to iterate to the next A-line of the image frame. Once all A-lines of the image frame have been processed, the clearing information for the entire image frame may be aggregated at Block 834, and at Block 836 the aggregated clearing information may be used in the flow diagram 600 so as to be processed at Block 610 of FIG. 6 in the manner described above. Accordingly, the above-described flow diagrams allow for the detection of an initial clearing event and a final clearing event within the blood vessel, so as to identify the conditions whereby an OCT pullback procedure may be automatically initiated.

Non-Limiting Software Features and Embodiments for Implementing the Disclosed Systems and Methods The description above is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic device, network PCs, minicomputers, mainframe computers, and the like. The disclosure can also be practiced in distributed computing environments where tasks are performed by remote processing devices that are linked through a communications network such as in different rooms of a catheter or cath lab.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods steps or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "searching" or "detecting" or "measuring" or "calculating" or "comparing" "generating" or "determining" or "displaying," Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The present disclosure, in some embodiments, also relates to apparatus for performing the operations herein. This apparatus may be specially constructed for the required purposes, or it may comprise a general purpose computer selectively activated or reconfigured by a computer program stored in the computer.

Embodiments of the disclosure may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other programmable logic device), discrete components, integrated circuitry (e.g., an Application Specific Integrated Circuit (ASIC)), or any other means including any combination thereof. In a typical embodiment of the present disclosure, some or all of the processing of the data collected using an OCT probe and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating imaging data, detecting vessel borders, detecting stent struts, comparing measured distances relative to set thresholds, and otherwise performing image comparison, signal processing, vessel detection, and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, IVUS scan data, interferometer signal data, target stent profiles, post-stent deployment lumen profiles and images, interpolated lumen profile views indicative of fully expanded stents, ratios of geometric values of expanded stent-based lumen profile to fully expanded lumen profile, stent expansion level indicia (color, hatching, etc.), highlighting/emphasizing pixel properties, side branch locations, side branch diameters, stent expansion percentages or fractions, pre-stenting FFR values, post-stenting FFR values, and other pre and post stenting values and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" or "substantially" is before a quantitative value, the present teachings also include the specific quantitative value itself, unless specifically stated otherwise. The terms "about" and "substantially" as used herein, refer to variations in a numerical quantity that can occur, for example, through measuring or handling procedures in the real world; through inadvertent error in these procedures; through differences/faults in the manufacture of materials, such as composite tape, through imperfections; as well as variations that would be recognized by one in the skill in the art as being equivalent so long as such variations do not encompass known values practiced by the prior art. Typically, the terms "about" and "substantially" means greater or lesser than the value or range of values stated by $\frac{1}{10}$ of the stated value, e.g., ±10%.

It should be understood that the order of steps or order for performing certain actions is immaterial so long as the present teachings remain operable. Moreover, two or more steps or actions may be conducted simultaneously.

It is to be understood that the figures and descriptions of the disclosure have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

What is claimed is:

1. A method of identifying blood clearing within a lumen comprising:
   accessing, by one or more processors, a plurality of intravascular image frames of a lumen;
   calculating, by the one or more processors, an average edge offset for a plurality scanlines within the plurality of intravascular image frames;
   identifying, by the one or more processors, a first clearing event based the average edge offset for a first set of image frames increasing in accordance with one or more initial conditions;
   identifying, by the one or more processors, a second clearing event based on the occurrence of the first clearing event and based on the average edge offset of a second set of image frames having not increased in accordance with one or more final conditions.

2. The method of claim 1 further comprising automatically initiating, by the one or more processors, a catheter pullback procedure based on the identification of the second clearing event and based on identification that the lumen is in a sufficiently-cleared state.

3. The method of claim 1, wherein the one or more initial conditions comprise at least one of the following:
   1) a short-term time-windowed average edge offset is larger than a predetermined maximum value; and
   2) the short-term time-windowed average edge offset is greater than a baseline time-windowed average edge offset by at least a particular offset amount.

4. The method of claim 3, wherein the predetermined maximum value is larger than a maximum catheter outer diameter offset.

5. The method of claim 3, wherein the particular offset amount is 40 microns.

6. The method of claim 3, wherein the short-term time-windowed average edge offset is calculated using a predetermined number of recently captured image frames.

7. The method of claim 3, wherein the baseline time-windowed average edge offset is calculated using image frames captured over a period of time that is greater than 0.5 seconds.

8. The method of claim 1, wherein the one or more final conditions comprise at least one of the following:
   1) a per-frame increment of an intermediate time-windowed average edge offset is less than a maximum per-frame increment of the intermediate time-windowed average edge offset for image frames captured after the first clearing event; and
   2) a predetermined period of time has passed since a largest clearing area has been observed in one or more of the plurality of image frames.

9. The method of claim 8, wherein the intermediate time-windowed average edge offset is based on image frames captured over a period of time that is less than 0.5 seconds.

10. The method of claim 8, wherein the largest clearing area is based on an average edge offset for one or more image frames and wherein the predetermined period of time is at least 40 seconds.

11. The method of claim 1 further comprising computing, by the one or more processors, an edge threshold based on identification of a minimum pixel intensity value and a maximum pixel intensity value over ranges of the scanlines for one or more image frames.

12. The method of claim 11 wherein the plurality of intravascular images are captured by a catheter devices having a sheath with a clear layer and a doped layer, and wherein computing the edge threshold comprises identifying the minimum pixel intensity value within a scanline range corresponding to the clear layer and identifying the maximum pixel intensity value within a scanline range corresponding to the doped layer.

13. The method of claim 1, further comprising identifying, by the one or more processors, edges within the plurality of intravascular image frames based on identification of at least one pixel intensity value of a selected scanline having an intensity that is greater than a first edge threshold and based on identification of at least one pixel intensity value of the selected scanline having an intensity value less than a second edge threshold, wherein the first edge threshold is greater than the second edge threshold.

14. A system of identifying blood clearing within a lumen comprising:
   a memory for storing image frame data:
   and one or more processors in communication with the memory, the one or more processors being operable to:
   access a plurality of intravascular image frames of a lumen;
   calculate an average edge offset for a plurality scanlines within the plurality of intravascular image frames;
   identify a first clearing event based the average edge offset for a first set of image frames increasing in accordance with one or more initial condition;

identify a second clearing event based on the occurrence of the first clearing event and based on the average edge offset of a second set of image frames having not increased in accordance with one or more final conditions.

15. The system of claim 14, wherein the one or more processors are further configured to automatically initiate a catheter pullback procedure based on the identification of the second clearing event and based on identification that the lumen is sufficiently-cleared.

16. The system of claim 14, wherein the one or more initial conditions comprise at least one of the following:
  1) a short-term time-windowed average edge offset is larger than a predetermined maximum value; and
  2) the short-term time-windowed average edge offset is greater than a baseline time-windowed average edge offset by at least a particular offset amount.

17. The system of claim 16, wherein the predetermined maximum value is larger than a maximum catheter outer diameter offset.

18. The system of claim 16, wherein the particular offset amount is 40 microns.

19. The system of claim 16, wherein the short-term time-windowed average edge offset is calculated using a predetermined number of recently captured image frames.

20. The system of claim 16, wherein the baseline time-windowed average edge offset is calculated using image frames captured over a period of time that is greater than 0.5 seconds.

21. The system of claim 14, wherein the one or more final conditions comprise at least one of the following:
  1) a per-frame increment of an intermediate time-windowed average edge offset is less than a maximum per-frame increment of the intermediate time-windowed average edge offset for image frames captured after the first clearing event; and
  2) a predetermined period of time has passed since a largest clearing area has been observed in one or more of the plurality of image frames.

22. The system of claim 21, wherein the intermediate time-windowed average edge offset is based on image frames captured over a period of time that is less than 0.5 seconds.

23. The system of claim 21, wherein the largest clearing area is based on an average edge offset for one or more image frames and wherein the predetermined period of time is at least 40 seconds.

24. The system of claim 14, wherein the one or more processors are further configured to compute an edge threshold based on identification of a minimum pixel intensity value and a maximum pixel intensity value over ranges of the scanlines for one or more image frames.

25. The system of claim 24 wherein the plurality of intravascular images are captured by a catheter devices having a sheath with a clear layer and a doped layer, and wherein computing the edge threshold comprises identifying the minimum pixel intensity value within a scanline range corresponding to the clear layer and identifying the maximum pixel intensity value within a scanline range corresponding to the doped layer.

26. The system of claim 1, wherein the one or more processors are further configured to identify, by the one or more processors, edges within the plurality of intravascular image frames based on identification of at least one pixel intensity value of a selected scanline having an intensity that is greater than a first edge threshold and based on identification of at least one pixel intensity value of the selected scanline having an intensity value less than a second edge threshold, wherein the first edge threshold is greater than the second edge threshold.

* * * * *